US00PP34327P2

(12) United States Plant Patent
Mathey

(10) Patent No.: US PP34,327 P2
(45) Date of Patent: Jun. 14, 2022

(54) ***HYDRANGEA* PLANT NAMED 'SMNHSME'**

(50) Latin Name: ***Hydrangea* sp.**
Varietal Denomination: SMNHSME

(71) Applicant: Spring Meadow Nursery Inc., Grand Haven, MI (US)

(72) Inventor: Megan Mathey, Holland, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/483,192

(22) Filed: Sep. 23, 2021

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Karen M Redden
(74) *Attorney, Agent, or Firm* — Cassandra Bright

(57) ABSTRACT

A new and distinct cultivar of *Hydrangea* plant named 'SMNHSME' is disclosed, characterized by large, mophead inflorescences, colored pastel pink to blue based on soil pH. Plants are very floriferous, have rounded dwarf habits and are densely branched. The new variety is a *Hydrangea*, typically produced as an outdoor ornamental plant.

4 Drawing Sheets

Latin name of the genus and species: *Hydrangea* sp.
Variety denomination: 'SMNHSME'.

BACKGROUND OF THE INVENTION

The new cultivar is a product of a planned breeding program conducted by the inventor, at a commercial nursery in Grand Haven, Mich. The objective of the breeding program was to produce new, more floriferous *Hydrangea* varieties with better colors and habits. The crossing resulting in the new variety was made during the Summer of 2016.

The seed parent is the variety *Hydrangea serrata*, 'MAK20', U.S. Plant Pat. No. 24,820. The pollen parent is the variety *Hydrangea macrophylla*, 'SMNHMSIGMA', U.S. Plant Pat. No. 26,929.

The new variety was found and selected by the inventor in the Summer of 2017 at the same nursery in Grand Haven, Mich.

Asexual reproduction of the new cultivar 'SMNHSME' was first performed during the Summer of 2017 in Grand Haven, Mich., by softwood cuttings. Through subsequent propagation, multiple additional generations have been reproduced, having shown that the unique features of this cultivar are stable and reproduced true to type.

SUMMARY OF THE INVENTION

The cultivar 'SMNHSME' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHSME.' These characteristics in combination distinguish 'SMNHSME' as a new and distinct *Hydrangea* cultivar:

1. Large mophead inflorescences.
2. Very floriferous, with inflorescences on nearly every lateral branch.
3. Remontant.
4. Dwarf size.
5. Densely branching, rounded/mounded habit.
6. Pastel pink and blue flower color, based on soil pH and presence/absence of aluminum.

PARENT COMPARISONS

Plants of 'SMNHSME' are similar to plants of the seed parent in most horticultural characteristics, however, plants of 'SMNHSME' differ in the following:

1. Inflorescences of 'SMNHSME' mophead, while inflorescences of the seed parent are lace-cap.
2. 'SMNHSME' has a lighter flower color, while the seed parent has a more vibrant flower color.

Plants of 'SMNHSME' are similar to plants of the pollen parent in most horticultural characteristics, however, plants of 'SMNHSME' differ in the following:

1. Plants of 'SMNHSME' have larger mophead inflorescences than the pollen parent.
2. 'SMNHSME' has lighter pink flowers in soil without bluing agent, while the pollen parent's flowers have a richer pink color in soil without bluing agent.
3. 'SMNHSME' has lighter blue flowers in soil with bluing agent than the pollen parent.
4. 'SMNHSME' produces more blooms than the pollen parent.

COMMERCIAL COMPARISON

Plants of the new cultivar *Hydrangea* 'SMNHSME' can be compared to the commercial variety *Hydrangea* 'SMNHSC', U.S. Plant Pat. No. 33,206. Plants of 'SMNHSME' are similar to plants of 'SMNHSC' in most horticultural characteristics, however, plants of 'SMNHSME' differ in the following:

1. 'SMNHSME' has light blue flower color in acidic soil with bluing agent, while 'SMNHSC' has lavender flower color in acidic soil with bluing agent.
2. 'SMNHSME' has soft pink flower color in basic soil without bluing agent, while 'SMNHSC' has hot pink flower color in basic soil without bluing agent.

BRIEF DESCRIPTION OF THE PHOTOGRAPHS

'SMNHSME' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years.

FIG. 1 shows a container grown plant of 'SMNHSME' grown in a greenhouse in Grand Haven, Mich. in 2020 at about 1.5 years of age. Plants have been treated with a typical acidic "bluing"(aluminum sulfate) treatment. Inflorescences shown are in a variety of stages of maturity.

DETAILED BOTANICAL DESCRIPTION

Figure 1:
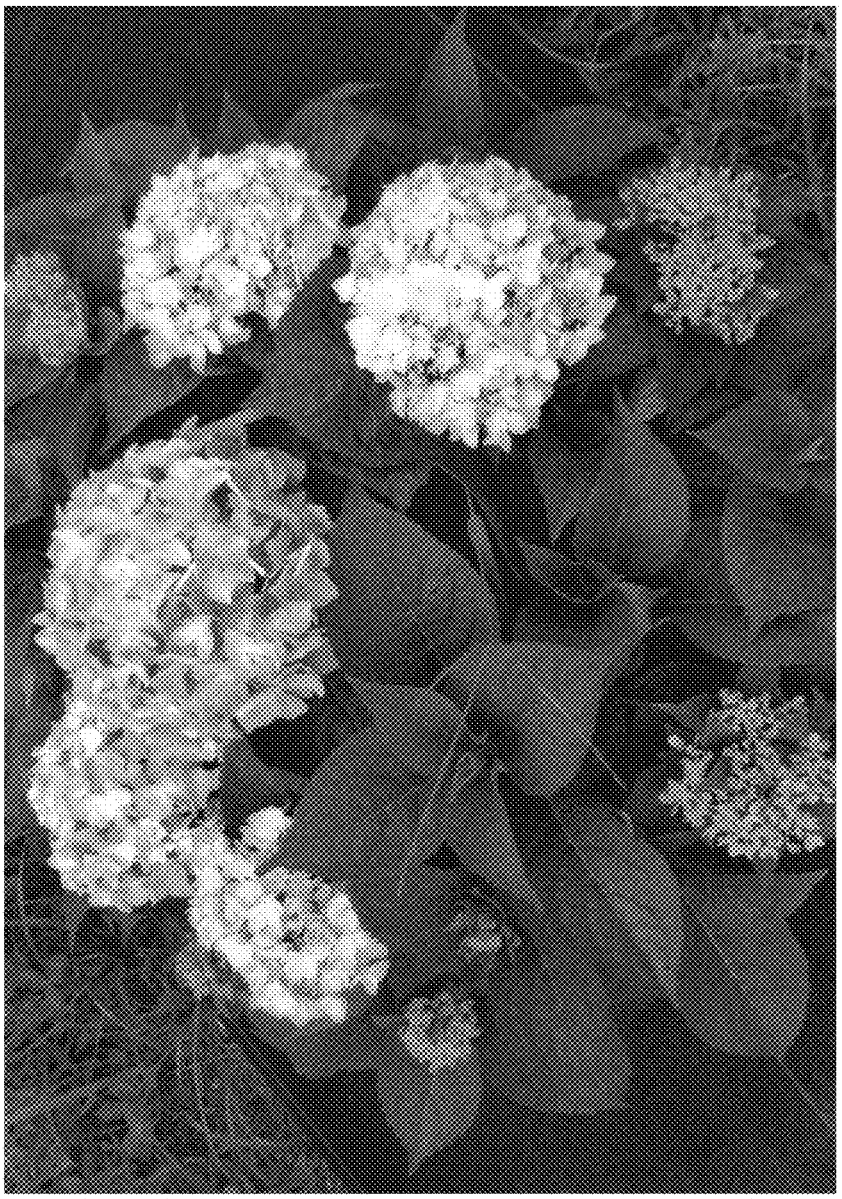
Figure 2:
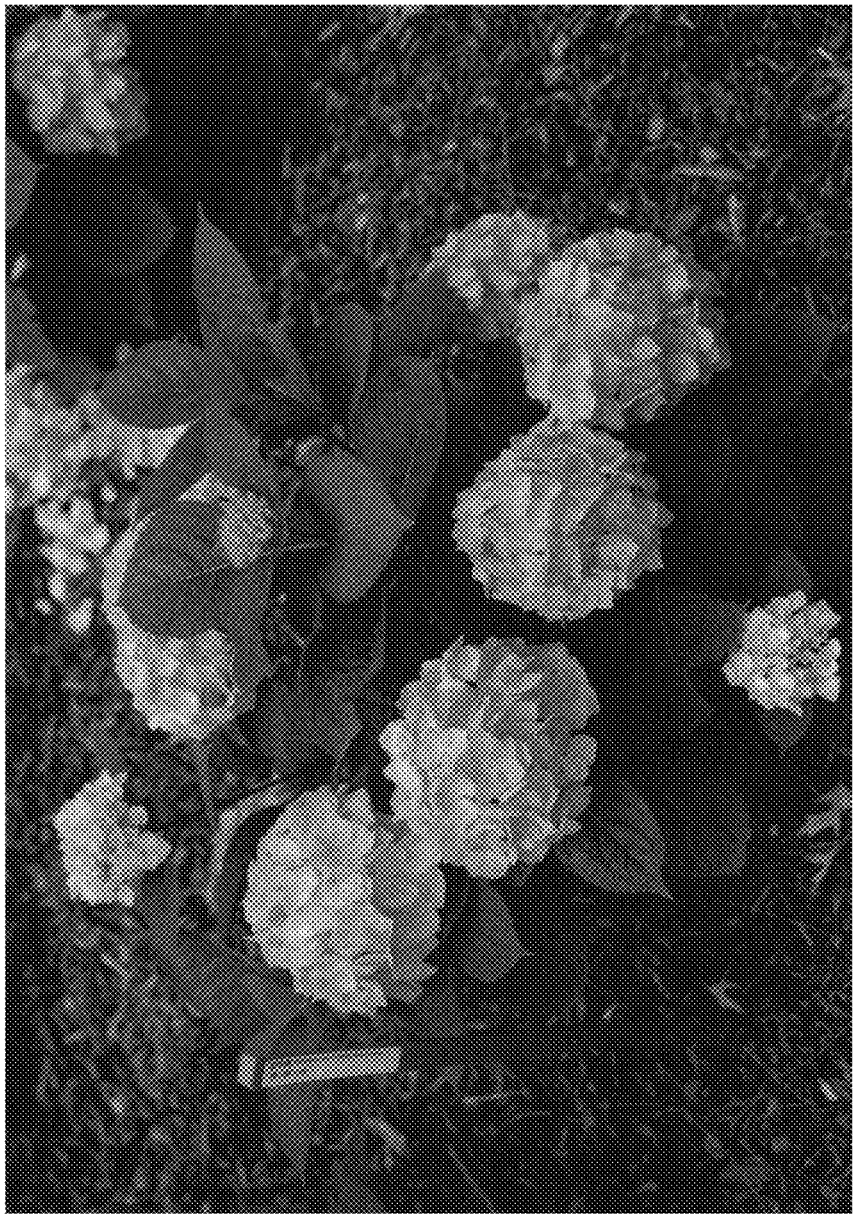
FIG. 2 shows a field grown plant of 'SMNHSME' with mature and immature inflorescences. No "bluing" treatment was given.
Figure 3:
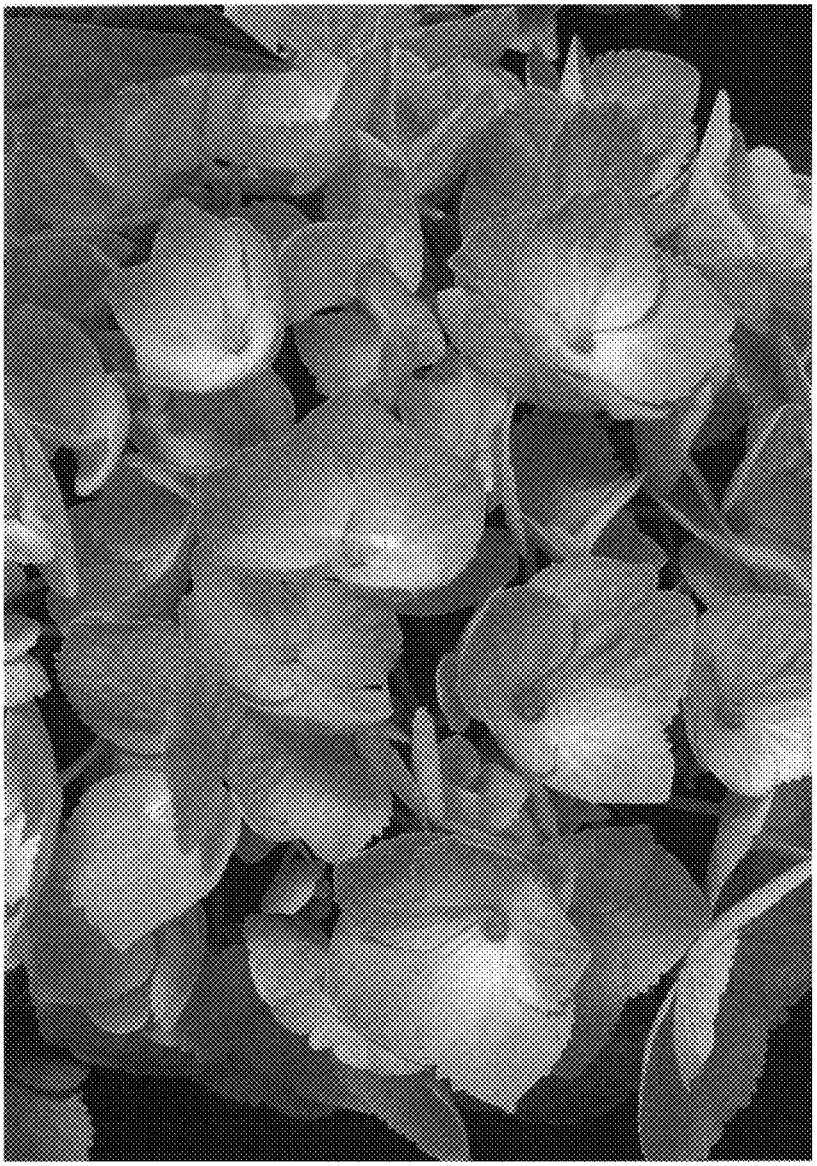
FIG. 3 shows the mature inflorescence of a container-grown plant of 'SMNHSME', treated without "bluing" treatment, grown in a greenhouse in Grand Haven, Mich. in 2019.
Figure 4:
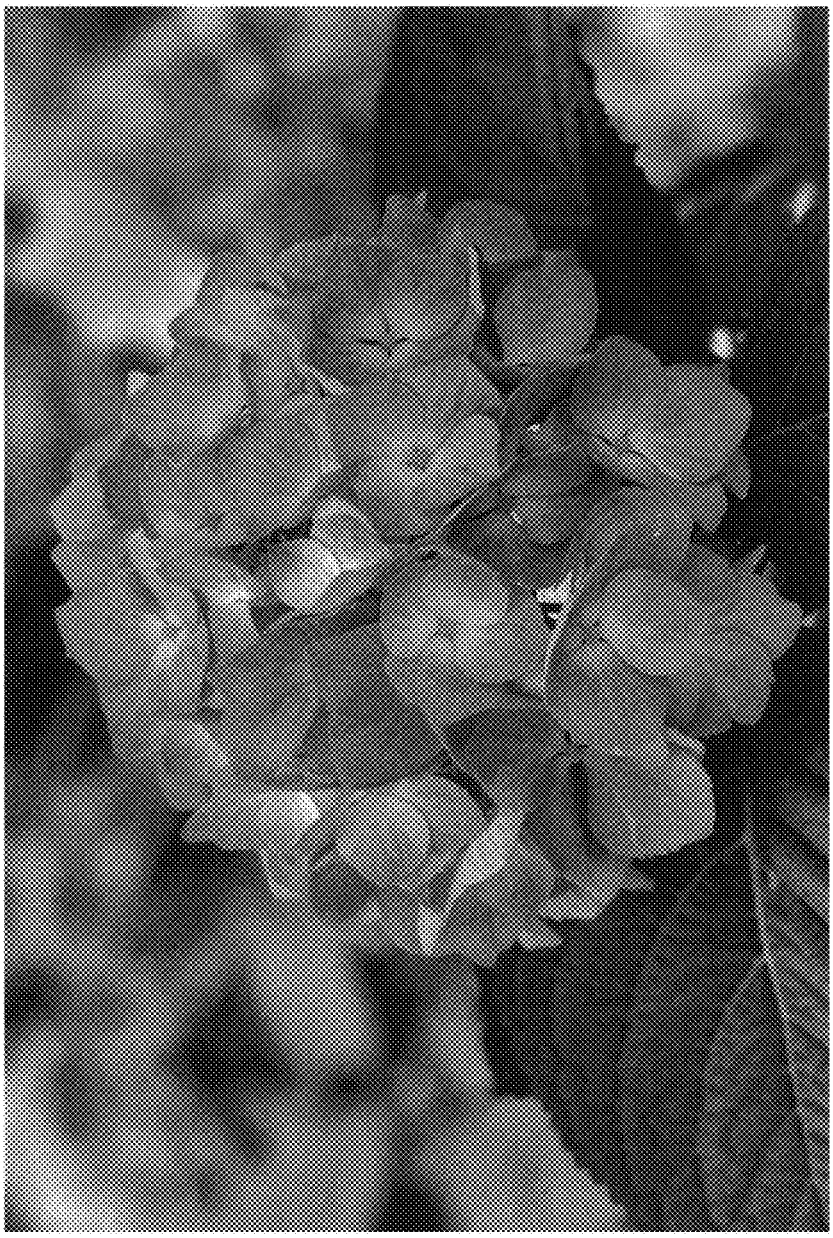
FIG. 4 shows the mature inflorescence of a container-grown plant, treated with a typical acidic "bluing"(aluminum sulfate) treatment, grown in a greenhouse in Grand Haven, Mich. in 2019.

In the following description, color references are made to The Royal Horticultural Society Colour Chart 2015, except where general terms of ordinary dictionary significance are used. The following observations and measurements describe 'SMNHSME' plants grown outdoors in Grand Haven, Mich. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: *Hydrangea* sp. 'SMNHSME'.

PROPAGATION

Typical method: Softwood cuttings.
Root initiation: 10 days.
Time to produce rooted cutting: 30 days during the Summer.
Roots: Medium to thick, moderately free branching, fibrous and fleshy, moderately dense. White in color, not accurately measured with RHS chart.

PLANT

Growth habit: Upwards and outwards.
Shape: Rounded.
Height: 50 cm.
Plant spread: 70 cm.
Pot size of plant described: 3 gallon container.
Age of plant described: Approximately 2 to 3 years.
Growth rate: Good.
Plant vigor: Moderate.
Stem:
- *Branching.*—Basal.
- *Number of lateral branches.*—About 25.
- *Shape.*—Round with lenticels.
- *Color.*—Immature: RHS Yellow-Green 144A to Green 143C. Mature: RHS Yellow-Green 144A to Green 143C, with Greyed-Orange 166A lenticels.
- *Length.*—40 cm.
- *Width.*—5 mm.
- *Aspect.*—60 to 80°.
- *Strength.*—Strong.
- *Pubescence.*—Slightly velvety, near inflorescence.
- *Internode length.*—6 to 8 cm.

FOLIAGE

Leaf:
- *Arrangement.*—Opposite.
- *Shape.*—Ovate to orbicular.
- *Length.*—9 to 12 cm.
- *Width.*—6.5 to 9.5 cm.
- *Apex.*—Acuminate.
- *Base.*—Obtuse.
- *Margin.*—Serrulate.
- *Texture of top surface.*—Smooth, coriaceous.
- *Texture of bottom surface.*—Smooth, coriaceous, with ribbing from veins.
- *Pubescence.*—None.
- *Color.*—Young foliage upper side: RHS Green 137B. Young foliage under side: RHS Yellow-Green 147B. Mature foliage upper side: RHS Green 137B. Mature foliage, under side: RHS Yellow-Green 147B.

Venation:
- *Type.*—Pinnate.
- *Color.*—Upper side: RHS Yellow-Green 147B, with tints of Greyed-Orange 166A. Under side: RHS Yellow-Green 147B.

Petiole:
- *Length.*—2 cm.
- *Width.*—2.5 mm.
- *Color.*—Upper side: RHS Yellow-Green 147B, with tints of Greyed-Orange 166A. Under side: RHS Yellow-Green 147B.
- *Texture.*—Upper side: Glabrous. Under side: Glabrous.

INFLORESCENCE

Natural flowering season: Early to late Summer.
Inflorescence type: Mophead.
Panicle:
- *Shape.*—Round, orbital.
- *Height.*—11 cm.
- *Diameter.*—17 cm.

Fragrance: None.
Sterile flowers:
- *Flowers per inflorescence.*—200 to 300+.
- *Aspect.*—Upright and outward.
- *Shape.*—Whorl.
- *Length.*—3.5 cm.
- *Diameter.*—3.5 cm.
- *Depth.*—2 mm.
- *Persistent or self-cleaning.*—Persistent.

Bud:
*Length.*—2 mm.
*Bud diameter.*—2 mm.
*Bud shape.*—Obovate.
*Bud color.*—RHS Yellow-Green 145A.
Petals:
*Number per Flower.*—5.
*Arrangement.*—Whorl.
*Shape.*—Ovate.
*Tip.*—Acute.
*Base.*—Obtuse.
*Margin.*—Entire.
*Length.*—3 mm.
*Width.*—2 mm.
*Texture.*—Upper side: Smooth. Under side: Smooth.
*Color.*—When Opening, Upper side: Acidic: RHS Blue 100C. Basic: RHS Greyed-Purple 186D. When Opening, Under side: Acidic: RHS Blue 100D. Basic: RHS Purple 75D. Fully Opened, Upper side: Acidic: RHS Blue 100C. Basic: RHS Greyed-Purple 186D. Fully Opened, Under side: Acidic: RHS Blue 100D. Basic: RHS Purple 75D.
Sepal:
*Number.*—3 to 5.
*Arrangement.*—Whorl.
*Shape.*—Ovate.
*Tip.*—Acute.
*Base.*—Obtuse.
*Margin.*—Irregular-subentire to sinuate, dentate.
*Length.*—2 to 2.5 cm.
*Width.*—2.5 to 3 mm.
*Texture.*—Upper side: Smooth. Under side: Smooth.
*Color.*—When Opening, Upper side: Acidic: RHS Violet-Blue 91C, with Yellow-Green 150C near center. Basic: RHS Greyed-Purple 186D, with Yellow-Green 150C near center. When Opening, Under side: Acidic: RHS Violet-Blue 91C, with Yellow-Green 150C near center. Basic: RHS Greyed-Purple 186D, with Yellow-Green 150C near center. Fully Opened, Upper side: Acidic: RHS Violet-Blue 97A. Basic: RHS Red-Purple 70. Fully Opened, Under side: Acidic: RHS Violet-Blue 95D. Basic: RHS Greyed-Purple 186D. Fading, Upper side: Acidic: RHS Violet-Blue 97A. Basic: RHS Purple 75B. Fading, Under side: Acidic: RHS Violet-Blue 95D. Basic: RHS Greyed-Purple 186D.
Pedicel:
*Length.*—2 cm.
*Diameter.*—2 mm.
*Angle.*—15-45°.
*Strength.*—Moderately strong.
*Texture.*—Some pubescence (slight and velvety).
*Color.*—Acidic: RHS Violet-Blue 94C-D. Basic: RHS Greyed-Purple 186D.
Fertile flowers:
*Flowers per inflorescence.*—About 150.
*Aspect.*—Upright.
*Shape.*—Rotate.
*Length.*—7 mm.
*Diameter.*—7 mm.
*Depth.*—5 mm.
*Persistent or self-cleaning.*—Self-cleaning.
Bud:
*Length.*—2 mm.
*Bud diameter.*—2 mm.
*Bud shape.*—Obovate.
*Bud color.*—RHS Yellow-Green 145A.
Petals:
*Number per flower.*—5.
*Arrangement.*—Whorl.
*Shape.*—Ovate.
*Tip.*—Acute.
*Base.*—Obtuse.
*Margin.*—Entire.
*Length.*—3 mm.
*Width.*—2 mm.
*Texture.*—Upper side: Smooth. Under side: Smooth.
*Color.*—When Opening, Upper side: Acidic: RHS Blue 100C. Basic: RHS Greyed-Purple 186D. When Opening, Under side: Acidic: RHS Blue 100D. Basic: RHS Purple 75D. Fully Opened, Upper side: Acidic: RHS Blue 100C. Basic: RHS Greyed-Purple 186D. Fully Opened, Under side: Acidic: RHS Blue 100D. Basic: RHS Purple 75D.
Sepal: None.
Pedicel:
*Length.*—3 to 4 mm.
*Diameter.*—1 mm.
*Angle.*—45°.
*Strength.*—Good.
*Texture.*—Glabrous.
*Color.*—Acidic: RHS Greyed-Purple N187B-C. Basic: RHS Red-Purple 70C.

REPRODUCTIVE ORGANS

Sterile flower:
Stamens:
*Number.*—About 10.
*Filament color.*—Acidic: RHS Blue 101A. Basic: RHS Red-Purple 70B.
*Filament length.*—4 mm.
Anthers:
*Length.*—1 mm.
*Shape.*—Round, bi-lobed, basifixed.
*Color.*—Acidic: RHS Blue 100B. Basic: RHS Red-Purple 70B.
*Pollen.*—Moderate.
*Pollen color.*—RHS Yellow-White 158C.
Pistil:
*Number.*—1.
*Length.*—2 mm.
Stigma:
*Shape.*—Lobed (3 to 4).
*Color.*—Acidic: RHS Blue 101B. Basic: RHS Red-Purple 70C.
*Style length.*—1 mm.
*Style color.*—Acidic: RHS Blue 101B. Basic: RHS Red-Purple 70C.
Fertile flower:
Stamen:
*Number.*—About 10.
*Filament length.*—4 mm.
*Filament color.*—Acidic: RHS Blue 101A. Basic: RHS Red-Purple 70B.
Anther:
*Shape.*—Round, bi-lobed, basifixed.
*Length.*—1 mm.
*Color.*—Acidic: RHS Blue 100B. Basic: RHS Red-Purple 70B.

*Pollen amount.*—Moderate.

*Pollen color.*—RHS Yellow-White 158C.

Pistil:

*Number.*—1.

*Length.*—2 mm.

Stigma:

*Shape.*—Lobed (3 to 4).

*Color.*—Acidic: RHS Blue 101B. Basic: RHS Red-Purple 70C.

*Style length.*—1 mm.

*Style color.*—Acidic: RHS Blue 101B. Basic: RHS Red-Purple 70C.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −32° C. and tolerates an upper temperature range to at least 36° C.

Fruit/seed production: Not observed to date.

What is claimed is:

1. A new and distinct cultivar of *Hydrangea* plant named 'SMNHSME' as herein illustrated and described.

* * * * *